US00PP30648P3

(12) United States Plant Patent
Snijder

(10) Patent No.: US PP30,648 P3
(45) Date of Patent: Jul. 2, 2019

(54) ***PELARGONIUM* PLANT NAMED 'PEQZ0039'**

(50) Latin Name: *Pelargonium interspecific*
Varietal Denomination: PEQZ0039

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,985

(22) Filed: Jun. 4, 2018

(65) Prior Publication Data

US 2019/0124812 P1 Apr. 25, 2019

(30) Foreign Application Priority Data

Oct. 23, 2017 (QZ) ..... PBR 2017/2680

(51) Int. Cl.
*A01H 5/02* (2018.01)
*A01H 6/42* (2018.01)

(52) U.S. Cl.
USPC ..... Plt./324
CPC ..... *A01H 6/425* (2018.05); *A01H 5/02* (2013.01)

(58) Field of Classification Search
USPC ..... Plt./324, 325, 329, 332
CPC ..... A01H 6/42; A01H 5/0277
See application file for complete search history.

*Primary Examiner* — Kent L Bell
(74) *Attorney, Agent, or Firm* — Dale Skalla

(57) ABSTRACT

A new *Pelargonium* plant named 'PEQZ0039' particularly distinguished by the light lavender inflorescences held above the dark green foliage, very heat and drought tolerant with continuous color through the most extreme summer heat, and a well-branched spreading plant habit.

1 Drawing Sheet

Latin name of the genus and species of the plant claimed: *Pelargonium interspecific.*

Varietal denomination: 'PEQZ0039'.

BACKGROUND OF THE NEW PLANT

The present invention comprises a new *Pelargonium*, botanically known as *Pelargonium interspecific*, and hereinafter referred to by the variety name 'PEQZ0039'.

'PEQZ0039' is a product of a planned breeding program. The new cultivar 'PEQZ0039' has light lavender inflorescences held above the dark green foliage, very heat and drought tolerant with continuous color through the most extreme summer heat, on a well-branched spreading plant habit.

'PEQZ0039' originates from a hybridization in a controlled breeding program made in February 2013 in a greenhouse in Enkhuizen, The Netherlands. The female parent was an unpatented, proprietary plant of *P. interspecific* parentage, identified as 'PEL-AZ3204-01' with white florets and longer peduncles when compared to 'PEQZ0039'.

The male parent of 'PEQZ0039' was an unpatented, proprietary plant of *P. interspecific* parentage, identified as 'PEI-AZ3206-02' with pink colored florets and a more dense plant habit when compared to 'PEQZ0039'. The resultant seed was sown in January 2014.

'PEQZ0039' was selected as one flowering plant within the progeny of the stated cross in June 2014 in a greenhouse in Enkhuizen, The Netherlands.

The first act of asexual reproduction of 'PEQZ0039' was accomplished when vegetative cuttings were propagated from the initial selection in July 2014 in a greenhouse in Enkhuizen, The Netherlands.

BRIEF SUMMARY OF INVENTION

Horticultural examination of plants grown from cuttings of the plant initiated in August 2014 in Enkhuizen, The Netherlands, and continuing thereafter, has demonstrated that the combination of characteristics as herein disclosed for 'PEQZ0039' are firmly fixed and are retained through successive generations of asexual reproduction.

'PEQZ0039' has not been observed under all possible environmental conditions. The phenotype may vary significantly with variations in environment such as temperature, light intensity, and day length.

A Plant Breeder's Right for this cultivar was applied for in the European Union on Oct. 23, 2017, No. 2017/2680. 'PEQZ0039' has not been made publicly available prior to the effective filing date of this application, notwithstanding any disclosure that may have been made less than one year prior to the effective filing date of this application by the inventor or another who obtained 'PEQZ0039' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawing shows typical flower and foliage characteristics of 'PEQZ0039' with colors being as true as possible with an illustration of this type.

Figure 1:
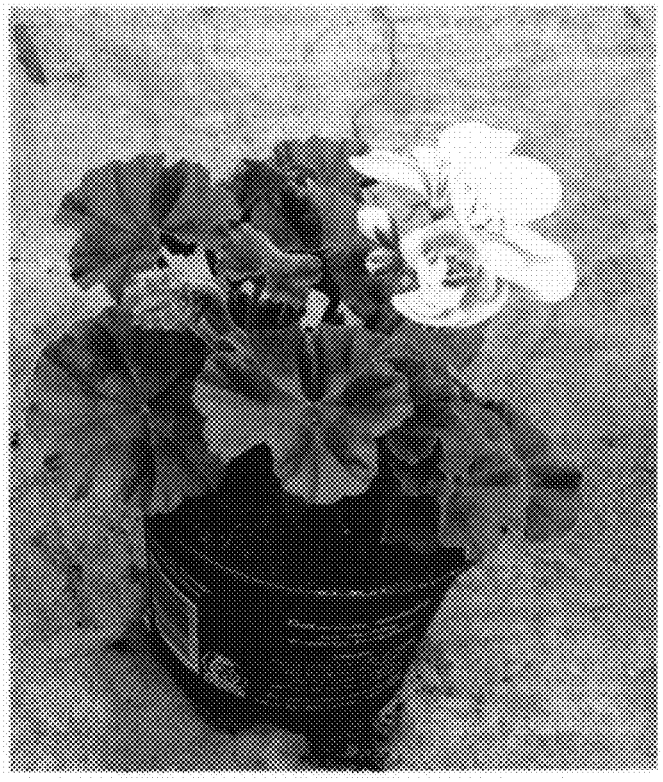
Figure 2:
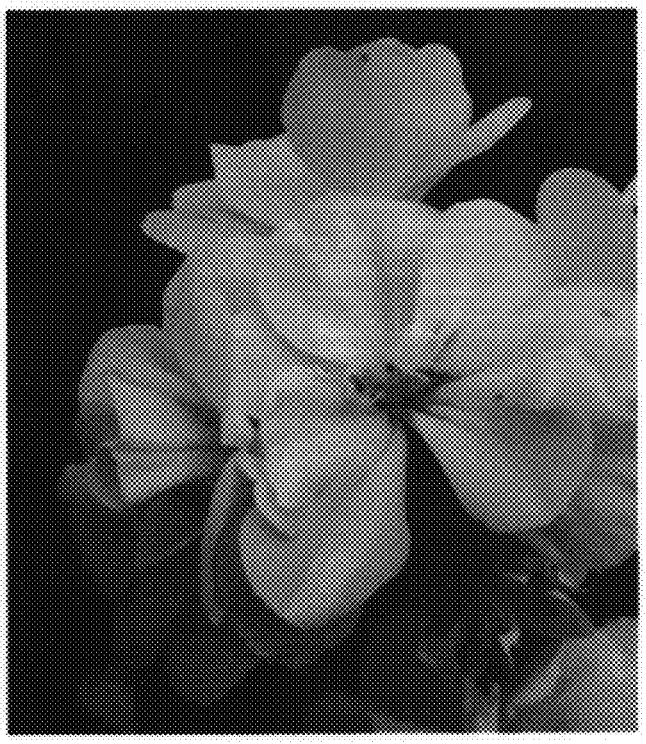

The photographic drawings show in FIG. 1, 1 flowering plant of the new variety and in FIG. 2, a close-up of an inflorescence.

DETAILED BOTANICAL DESCRIPTION

The plant descriptions and measurements were taken in Enkhuizen, The Netherlands in late October 2017 under natural light. These plants were approximately 22-24 weeks old and were grown in a 3 gallon pots, in an outdoors trial. The plant shown in FIG. 1 was about 14 weeks old growing in a 4 inch pot in a greenhouse. The photographs were taken in April 2017.

Color references are made to The Royal Horticultural Society Colour Chart (R.H.S.) 2001.

TABLE 1

DIFFERENCES BETWEEN THE NEW VARIETY 'PEQZ0039' AND A MOST SIMILAR VARIETY

| | 'PEQZ0039' | 'Fip-765' (U.S. Pat. No. PP14,083) |
|---|---|---|
| Anthocyanin coloration peduncle: | Weak | Very strong |

Plant:

*Form, growth and habit.*—Upright, outwardly spreading and rounded growth habit, heat and drought tolerant with continuous color through the most extreme summer heat, edema tolerance, well-branched plant habit.

*Plant height.*—24-25 cm.

*Plant height (inflorescence included).*—29-33 cm.

*Plant width.*—44-49 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—Closest to RHS 143A.

*Immature leaf, lower surface.*—Closest to RHS 143C.

*Mature leaf, color upper surface.*—Closest to RHS 147A.

*Mature leaf, color lower surface.*—Closest to RHS 147B (A bit RHS 146B), Veins RHS 147C.

*Length.*—6-8 cm.

*Width.*—7-9 cm.

*Shape.*—Cordate, a bit tridentate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 144A at base of leaf.

*Color of veins, lower surface.*—RHS 145B at base of leaf.

*Pattern of veining.*—Palmate.

*Petiole color.*—RHS 143C.

*Petiole length.*—6-9.0 cm.

*Diameter of petiole.*—0.3 cm.

*Texture.*—Pilose, hirsute, glandular hairs.

Stem:

*Quantity of branches.*—8-10.

*Color of stem.*—Between RHS 145A and RHS 145B.

*Length of stem.*—4-12 cm.

*Diameter.*—0.4-0.6 cm.

*Length of internodes.*—0.5-3 cm.

*Texture.*—Sparsely hirsute, pilose, glandular hairs.

Peduncle:

*Color of peduncle.*—RHS 147C.

*Length of peduncle.*—14-19 cm.

*Peduncle diameter.*—0.3-0.35 cm.

*Texture.*—Hirsute, glandular hairs.

Pedicel:

*Color of pedicel.*—RHS 145A.

*Length of pedicel.*—3-4 cm.

*Diameter of pedicel.*—0.15-0.2 cm.

*Texture.*—Sparsely pilose, glandular hairs.

Bud (just before opening):

*Color.*—Closest to RHS 49C.

*Length.*—1.5 cm.

*Width.*—0.9 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—32, with 15 immature umbels in various stages.

*Fragrance.*—None.

*Umbel diameter.*—12-14.0 cm.

*Umbel depth.*—6.5-7.5 cm.

Corolla:

*Form.*—Semi-double.

*Number of petals.*—Up to 12.

*Diameter of flower.*—4-5 cm.

*Depth of flower.*—1.8-2.2 cm.

*Color upper petals, upper surface.*—Closest to RHS 43B but brighter and deeper, with up to RHS 84A veining.

*Color upper petals, lower surface.*—Closest to RHS 85C, veins RHS 85B.

*Length of upper petals.*—2.7 cm.

*Width of upper petals.*—2.1 cm.

*Color lower petals, upper surface.*—Closest to RHS 72A to RHS 67C.

*Color lower petals, lower surface.*—RHS 84C.

*Length of lower petals.*—2.1 cm.

*Width of lower petals.*—2.3 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144A mottled with anthcyanins of about RHS 178B.

*Length of sepals.*—1-1.2 cm.

*Width of sepals.*—0.3-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.2 cm.

*Style color.*—RHS 145D.

*Style length.*—0.4-0.5 cm.

*Stigma color.*—Closest to RHS 157A.

*Ovary color.*—RHS 145B.

*Ovary length.*—0.4-0.5 cm.

*Ovary diameter.*—0.2 cm.

Androecium:

*Number of stamens.*—7.

*Color of filaments.*—Whiter than RHS 155D.

*Length filaments.*—0.4 cm.

*Anther color.*—RHS 61A.

*Length of anthers.*—0.2 cm.

*Color of pollen.*—RHS 169A.

*Pollen amount.*—Normal.

*Fertility/seed set.*—Has not been determined to date.

*Disease/pest resistance.*—Has not been determined to date.

What is claimed is:

1. A new and distinct variety of *Pelargonium* plant named 'PEQZ0039' substantially as illustrated and described herein.

* * * * *